United States Patent
Markovic

(10) Patent No.: US 7,041,301 B1
(45) Date of Patent: May 9, 2006

(54) INTERFERON IMMUNOTHERAPY

(75) Inventor: Svetomir N. Markovic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/187,385

(22) Filed: Nov. 6, 1998

Related U.S. Application Data

(60) Provisional application No. 60/064,618, filed on Nov. 7, 1997.

(51) Int. Cl.
*A61K 45/00* (2006.01)

(52) U.S. Cl. .................. 424/278.1; 424/85.4; 424/85.1; 424/85.2; 424/85.7; 530/351; 514/2

(58) Field of Classification Search ................ 530/351; 514/2; 424/278.1, 85.4, 85.1, 85.2, 85.7
See application file for complete search history.

(56) References Cited

U.S. PATENT DOCUMENTS

| | | | | |
|---|---|---|---|---|
| 4,846,782 | A | | 7/1989 | Bonnem .................... 600/1 |
| 5,997,858 | A | * | 12/1999 | Tovey et al. |
| 6,063,373 | A | * | 5/2000 | Hellstrand et al. ......... 424/85.2 |

OTHER PUBLICATIONS

Kokoschka, E.-M. et al., J. Invest. Dermatol. 95: 193S-197S, 1990.*
Nichols, P.H. et al. Clin. Exp. Immunol. 94: 4-10, 1993.*
Brittenden, J. et al. Natural Killer Cells and Cancer. Cancer, 77(7): 1226-1243, Apr., 1996.*
Lennard, T.W.J. et al. the influence of surgical operations on components of the human immune system. Br. J. Surg., 72: 771-776, 1985.*
Roitt, I.M. et al. Immunology. 3rd Edition, Mosby, St. Louis, pp. 2.5-2.7, 1993.*
Illustrated Stedman's Medical Dictionary, 24th Edition, Williams & Wilkins, Baltimore, p. 707, 1982.*
Ibayashi et al., "Regression of Pulmonary and Multiple Skeletal Metastases from Renal Cell Carcinoma by Nephrectomy and Alpha-interferon Therapy: A Case Report," *Jpn. J. Clin. Oncol.*, 1993, 23(6):378-383.
Mahvi et al., "Interferon α enhances expression of TAG-72 and carcinoembryonic antigen in patients with primary colorectal cancer," *Cancer Immunol. Immunother.*, 1995, 40:311-314.
Monkarsh et al., "Positional Isomers of Monopegylated Interferon α-2a: Isolation, Characterization, and Biological Activity," *Analytical Biochemistry*, 1997, 247:434-440.
Agarwala, S. et al., "Interferons in the Therapy of Solid Tumors," Oncology, 51:129-136 (1994).
Borden, E., "Interferons: Rationale for Clinical Trials in Neoplastic Disease," Annals of Internal Medicine, 91:472-479 (1979).
Brenner, B. et al., "Natural Killer Cell Function in Patients With Acquired Immunodeficiency Syndrome and Related Diseases," Journal of Leukocyte Biology, 46:75-83 (1989).
Burchell, J. et al., "Complexity of Expression of Antigenic Determinants, Recognized by Monoclonal Antibodies HMFG-1 and HFMG-2, In Normal and Malignant Human Mammary Epithelial Calls," The Journal of Immunology, 131(1):508-513 (1983).
Edwards, B. et al., "Comparative in Vivo and in Vitro Activation of Human Natural Killer Cells by Two Recombinant α-Interferons Differing in Antiviral Activity," Cancer Research, 44:3135-3139 (1984).
Edwards, B. et al., "Low Doses of Interferon Alpha Result in More Effective Clinical Natural Killer Cell Activation," J. Clin. Invest., 75:1908-1913 (1985).

(Continued)

*Primary Examiner*—Sheela J. Huff
(74) *Attorney, Agent, or Firm*—Fish & Richardson P.C., P.A.

(57) ABSTRACT

A method for reducing the recurrence of a resectable malignant tumor includes administering an immunostimulatory dosage of an α-interferon composition, then surgically resecting the malignant tumor. A method for treating a human patient having a non-resectable malignant tumor includes administering an immunostimulatory dosage of an α-interferon composition to the patient and treating the patient with effective non-surgical medical methodologies to diminish the tumor. An article of manufacture combines an α-interferon composition within a packaging material and a package label or insert indicating that administration of an immunostimulatory dosage of an α-interferon composition followed by surgical resection of a malignant tumor can be effective for treating a human patient having the malignant tumor.

3 Claims, 3 Drawing Sheets

OTHER PUBLICATIONS

Einhorn, S. et al., "Interferon and Natural Killer Activity in Multiple Myeloma . . . ," Int. J. Cancer, 30:167-172 (1982).

Einhorn, S. et al., "Interferon and Spontaneous Cytotoxicity in Man," Acta. Med. Scand., 204:477-483 (1978).

Golub, S. et al., "Systemic Administration of Human Leukocyte Interferon to Melanoma Patients . . . ," JNCI, 68(5):703-710 (1982).

Gresser, I. et al., "Mechanism of the Antitumour Effect of Interferon in Mice," Nature, 239:167-168 (1972).

Kalvakolanu, D. et al., "An Overview of the Interferon System: Signal Transduction and Mechanisms of Action," Cancer Investigation, 14(1):25-53 (1996).

Kopp, W. et al., "Immunological Monitoring and Clinical Trials of Biological Response Modifiers," Cancer Chemotherapy and Biological Response Modifiers, 15:226-286 (1994).

Krown, S. et al., "High-Dose Human Lymphoblastoid Interferon in Metastatic Colorectal Cancer: Clinical Results and Modification of Biological Responses," Cancer Treatment Reports, 71(1):39-45 (1987).

Kutza, J. et al., "The Effects of General Anesthesia and Surgery on Basal and Interferon Stimulated Natural Killer Cell Activity of Humans," Anesth. Analg., 85:918-923 (1997).

Laszlo, J. et al., "Phase I Study of Pharmacological and Immunological Effects of Human Lymphoblastoid Interferon Given to Patients with Cancer," Cancer Res., 43:4458-4466 (1983).

Lucero, M. et al., "Comparison of Effects of Leukocyte and Fibroblast Interferon on Immunological Parameters in Cancer Patients," Eur. J. Cancer Clin. Oncol., 18(3):243-251 (1982).

Maluish, A. et al., "Depression of Natural Killer Cytotoxicity After In Vivo Administration of Recombinant Leukocyte Interferon," The Journal of Immunology, 131(1):503-507 (1983).

Maffezzini, M., "Treatment of Advanced Metastatic Renal Cell Carcinoma With Recombinant Interleukin-2-Based Immunotherapy Regimens: The Restrictedness of the Results Should not Generate Disbelief," The Cancer Journal, 10(3):140-142 (1997).

Markovic, S. et al., "Anesthesia Inhibits Interferon-Induced Natural Killer Cell Cytotoxicity via Induction of $CD8^+$ Suppressor Cells," Cellular Immunology, 151:474-480 (1993).

Markovic, S. et al., "Anesthesia Inhibits Poly I:C Induced Stimulation of Natural Killer Cell Cytotoxicity in Mice," Clinical Immunology and Immunopathology, 56:202-209 (1990).

Markovic, S. et al., "Inhibition of Induction of Natural Killer Activity in Mice by General Anesthesia (Avertin): Role of Interferon," Clinical Immunology and Immunopathology, 60:181-189 (1991).

Markovic, S. et al., "Inhibition of Interferon Stimulation of Natural Killer Cell Activity in Mice Anesthetized with Halothane or Isoflurane," Anesthesiology, 78(4):700-706 (1993).

Markovic, S. et al., "Neoadjuvant Immunotherapy With Interferon of the Spontaneously Metastasizing Murine B16F10L Melanoma," Int. J. Cancer, 45:788-794 (1990).

Markovic, S. et al., "Role of Natural Killer and T-Cells in Interferon Induced Inhibition of Spontaneous Metastases of the B16F10L Murine Melanoma," Cancer Research, 51:1124-1128 (1991).

Neefe, J. et al., "Augmented Immunity in Cancer Patients Treated with α-Interferon," Cancer Research, 45:874-878 (1985).

Nichols, P. et al., "Peri-operative Modulation of Cellular Immunity in Patients with Colorectal Cancer," Clin. Exp. Immunol., 94:4-10 (1993).

Pape, G. et al., "Kinetics of Natural Cytotoxicity in Patients Treated with Human Fibroblast Interferon," Cancer Immunology and Immunotherapy, 11:1-6 (1981).

Rohatiner, A. et al., "Management of Follicular Lymphoma," Oncology, 6:473-479 (1994).

Sedman, P. et al., "Effects of Low Dose Perioperative Interferon on the Surgically Induced Suppression of Antitumour Immune Responses," Br. J. Surg., 75:976-981 (1988).

Seiden, M. et al., "Multiple Myeloma," Current Opinion in Oncology, 6:41-49 (1994).

Shapiro, R. et al., "Remission of Nephrotic Syndrome of HBV-Associated Membranous Glomerulopathy following Treatment with Interferon," Am. J. Nephrology, 15:343-347 (1995).

Toliou, Th. et al., "Natural Killer Cell Activation After Interferon Administration in Patients with Metastatic Renal Cell Carcinoma: An Ultrastructural and Immunohistochemical Study," Eur. Urol., 29:252-256 (1996).

Ucar R., et al., "Interferons: Their Role in Clinical Practice," Annals of Allergy Asthma & Immunology, 75:377-386 (1995).

Urabe, A., "Interferons for the Treatment of Hematological Malignancies." Oncology, 51:137-141 (1994).

* cited by examiner

US 7,041,301 B1

INTERFERON IMMUNOTHERAPY

CROSS REFERENCE TO RELATED APPLICATIONS

This patent application claims benefit of U.S. provisional application Ser. No. 60/064,618 filed Nov. 7, 1997.

FIELD OF THE INVENTION

The invention relates to administering interferon. More particularly, the invention relates to administering interferon preoperatively and administering interferon for treating cancer.

BACKGROUND OF THE INVENTION

Interferons (IFNs) are immunologically active proteins produced by mammalian cells following infectious or cytokine stimuli. As biologically active substances, IFNs have three broad modes of action: direct antiproliferative effects on tumor cells, direct antiviral effects inhibiting viral replication, and immunomodulatory (also referred to as immunostimulatory) effects on the mammalian immune system. Kalvakolanu, D. V., & Borden, B. C. *Cancer Investigation,* 14:25 (1996).

Interferons are generally divided into three species (IFN-$\alpha$, IFN-$\beta$ and IFN-$\gamma$) and two types according to their structural and functional characteristics. Type I IFNs (IFN-$\alpha$ and IFN-$\beta$) are produced following viral infection and have dosage dependent anti-tumor, anti-viral and immunomodulatory properties. Kopp, C. W. et al., *Cancer Chemotherapy and Biological Response Modifiers,* 15:226 (1994); Agrwala, S. S., & Kirkwood, M. J., *Oncology,* 51:129 (1994). Type II IFNs (IFN-$\gamma$) are produced by T lymphocytes following lymphokine stimulation. Kalvakolanu, V. D. & Borden, C. E., *Cancer Investigation,* 14:25 (1996). Type II IFNs have predominantly an immunomodulatory function with relatively less antiviral or antitumor activity.

Announced as a potential cure for cancer, IFNs have been used for treating several disease states, including chronic hepatitis C, multiple myeloma, multiple sclerosis, melanoma and CML. Kalvakolanu, V. D. & Borden, C. E., *Cancer Invest.,* 14:25 (1996); Mughal, T. I. & Goodman, J. M., *Ann. Onc.,* 6:537 (1995); Ucar, R. et al., *Ann. Allergy, Asthma &Immun.,* 75:377 (1995); Sapiro, R. J. et al., *Am. J. Nephr.,* 15:343 (1995); Sharara, A. I. et al., *Ann. Int. Med.,* 125:658 (1996).

The current standard of care for human IFN cancer therapies utilizes antiproliferative IFN dosages. These dosages are maximum tolerable dosages at about 10–20 million U/m$^2$ per day. Kirkwood, *J. Clin. Oncol.,* 14:7–17 (1996). IFN treatments have had limited effectiveness against solid tumors. Moreover, antiproliferative IFN dosages can suppress multiple immune system parameters including NK lymphocytes. Maluish et al., *J. Immun.,* 131:503 (1983).

Cancer therapy also includes surgical resection or debulking of a tumor mass. Surgical excision is not typically curative because surgery does not combat minimal residual disease. Minimal residual disease refers to cancer cells that have dissociated from a primary tumor either prior to surgery or during surgical resection. Current imaging techniques, such as CT scans and x-rays, are unable to detect these dissociated cancer cells. It is believed these dissociated cancer cells lead to primary tumor recurrence. Also, these undetected cells are the nidus of metastatic disease, which is considered the most significant component of cancer mortality.

To increase the cancer therapy success rate, chemical and immunological compounds are used in conjunction with surgical resection. Effective combined therapies are difficult to develop. One possible explanation for the lack of effective therapies is the phenomenon of transient postoperative immunological deficiencies observed for surgical patients. Slade et al., *Surgery,* 78: 363 (1975); Lee, Y. T., *J. Surg. Onc.,* 9:425–430 (1977). This postoperative immunosuppression increases a patient's susceptibility to post-operative infections, tumor reoccurrence and metastasis. As a result, the medical community is still searching for effective cancer therapies.

SUMMARY OF THE INVENTION

In one aspect, the invention is a method for treating a human patient having a malignant tumor by administering an immunostimulatory dosage of an $\alpha$-interferon composition to the patient, then surgically resecting the malignant tumor. The immunostimulatory dosage may be about 3,000,000 U/m$^2$ of $\alpha$-interferon per day or less. The immunostimulatory dosage can also be set at about 1,000,000 U/m$^2$ per day or less, about 500,000 U/m$^2$ per day or less, about 250,000 U/m$^2$ per day or less, or about 100,000 U/m$^2$ per day or less. The immunostimulatory dosage may also be about 3,000,000 U/m$^2$ of $\alpha$-interferon per day, about 1,000,000 U/m$^2$ per day, about 500,000 U/m$^2$ per day, about 250,000 U/m$^2$ per day, or about 100,000 U/m$^2$ per day. In one embodiment, the dosage is administered once per day, typically for about five days prior to resecting the malignancy.

The immunostimulatory dosage can be selected to increase a patient's NK lymphocyte cytotoxicity at least about 50% above the NK lymphocyte cytotoxicity level that the patient had before administering the $\alpha$-interferon composition. Preferably, the immunostimulatory dosage increases a patient's NK lymphocyte cytotoxicity at least about 75% above the NK lymphocyte cytotoxicity level that the patient had before administering the $\alpha$-interferon. The NK lymphocyte cytotoxicity can be measured at an effector to target cell ratio from about 15:1 to about 50:1. Other effector cell to target cell ratios can include 3:1, 6:1, 10:1, 12:1, 25:1, 50:1, 75:1, and 100:1. The immunostimulatory dosage may also increase B-lymphocyte and/or T-lymphocyte activation. The immunostimulatory dosage may also increase B-lymphocyte and/or T-lymphocyte function.

The method is useful for treating solid tumors, including without limitation breast cancer, lung cancer, pancreatic cancer, brain cancer, prostate cancer, ovarian cancer, uterine cancer, renal cancer, melanoma and other solid tumors. The method is particularly useful for treating melanoma and renal carcinoma tumors. In another embodiment, the solid tumor is an early-stage solid tumor.

In another aspect, the invention is a method for preventing post-operative infections by administering an immunostimulatory dosage of an $\alpha$-interferon composition to a human before surgery.

In another aspect, the invention is an article of manufacture encompassing packaging material and an $\alpha$-interferon composition contained within the packaging material. The packaging material includes a label or package insert indicating that administration of an immunostimulatory dosage of the $\alpha$-interferon composition followed by surgical resection of a malignant tumor can be effective for treating a human patient having a malignant tumor.

In another aspect, the invention features an article of manufacture containing packaging material and an $\alpha$-interferon composition contained within the packaging material. The packaging material can contain a label or package insert indicating that administration of an immunostimulatory dosage of the α-interferon composition in conjunction with treating the patient using effective non-surgical medical methodologies for diminishing the malignant tumor can be effective for treating a human patient having the malignant tumor.

In another aspect, the invention features a method for treating a human patient having a non-resectable malignant tumor by administering an immunostimulatory dosage of an α-interferon composition to the patient and treating the patient using effective non-surgical medical methodologies to diminish the tumor. In one embodiment, the medical methodologies include radiation therapy.

The immunostimulatory dosage may be about 3,000,000 U/m$^2$ of α-interferon per day or less. The immunostimulatory dosage can also be set at about 1,000,000 U/m$^2$ per day or less, about 500,000 U/m$^2$ per day or less, about 250,000 U/m$^2$ per day or less, or about 100,000 U/m$^2$ per day or less. The immunostimulatory dosage may also be about 3,000,000 U/m$^2$ of α-interferon per day, about 1,000,000 U/m$^2$ per day, about 500,000 U/m$^2$ per day, about 250,000 U/m$^2$ per day, or about 100,000 U/m$^2$ per day. In one embodiment, the dosage is administered once per day, typically for about five days prior to resecting the malignancy.

The immunostimulatory dosage can be selected to increase a patient's NK lymphocyte cytotoxicity at least about 50% above the NK lymphocyte cytotoxicity level that the patient had before administering the α-interferon composition. Preferably, the immunostimulatory dosage increases a patient's NK lymphocyte cytotoxicity at least about 75% above the NK lymphocyte cytotoxicity level that the patient had before administering the α-interferon. The NK lymphocyte cytotoxicity can be measured at an effector to target cell ratio from about 15:1 to about 50:1. Other effector cell to target cell ratios can include 3:1, 6:1, 10:1, 12:1, 25:1, 50:1, 75:1, and 100:1. The immunostimulatory dosage may also increase B-lymphocyte and/or T-lymphocyte activation. The immunostimulatory dosage may also increase B-lymphocyte and/or T-lymphocyte function.

The method is useful for treating solid tumors, including without limitation breast cancer, lung cancer, pancreatic cancer, brain cancer, prostate cancer, ovarian cancer, uterine cancer, renal cancer, melanoma and other solid tumors. The method is particularly useful for treating melanoma and renal carcinoma tumors. In another embodiment, the solid tumor is an early-stage solid tumor.

Advantages of the invention include eliminating, or inhibiting the progress of, minimal residual disease, which includes preventing both primary tumor regrowth and metastatic disease following surgical resection or other medical treatments.

Unless otherwise defined, all technical and scientific terms and abbreviations used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. Other features and advantages of the invention will be apparent from the following description of the preferred embodiments and from the claims.

DETAILED DESCRIPTION

Figure 1:
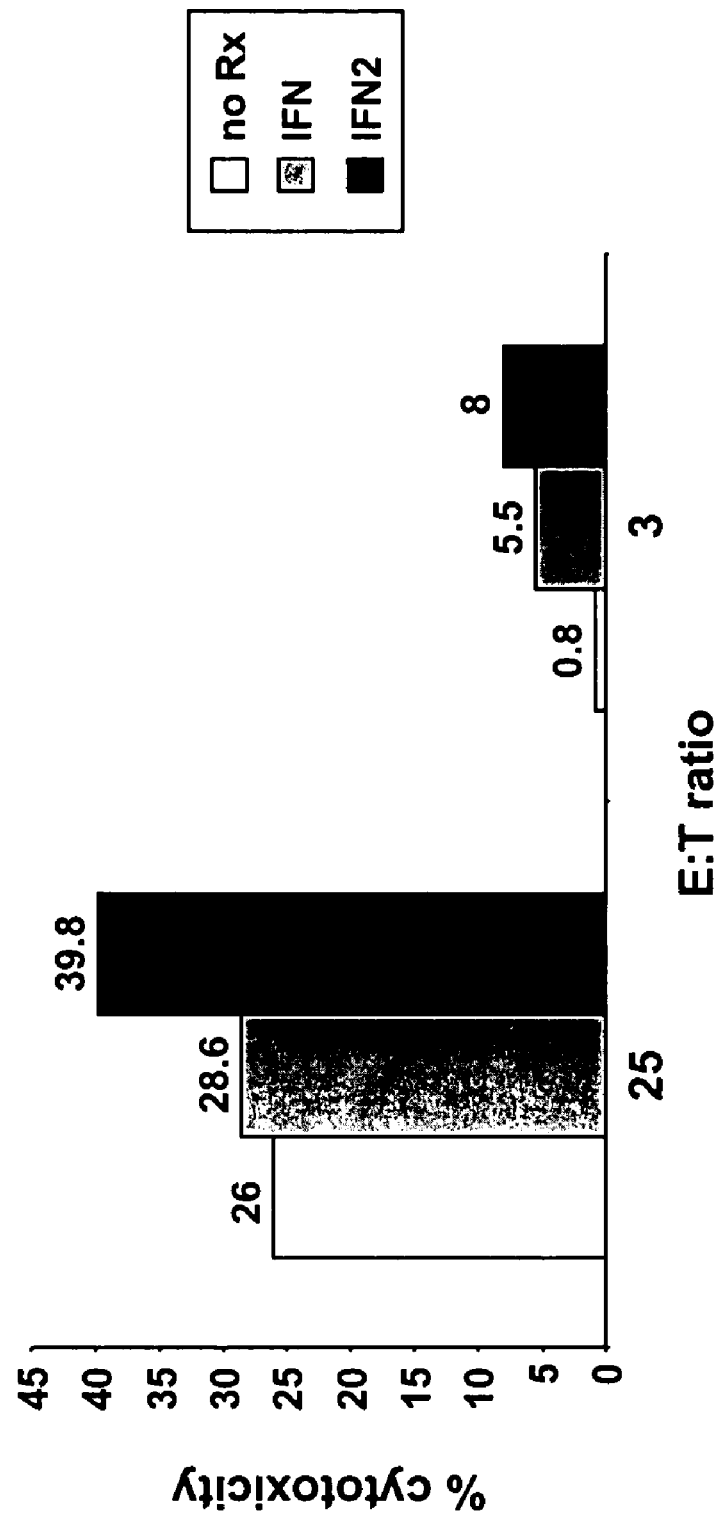
FIG. 1 is a graph depicting the increase in NK lymphocyte cytotoxicity levels at effector:target cell ratios of 3:1 and 25:1 after administering a low dosage of ALFERON-N™ to a human volunteer in vivo.

The present invention involves administering IFN-α to patients prior to surgically resecting a resectable malignancy, for reducing the risk of primary tumor recurrence, and for preventing the occurrence of metastases. The invention also involves administering IFN-α to patients prior to surgery to prevent post-operative infections and administering IFN-α to patients undergoing alternative methodologies for reducing, diminishing or eliminating solid malignancies.

Interferons can stimulate several cell types including Natural Killer (NK) lymphocytes. NK lymphocytes are a primary component of the mammalian immune system's defenses against infection and neoplastic diseases, and possess antitumor, antiviral and antibacterial properties. Administering mice IFN-α and IFN-β enhances the cytotoxic activities of NK lymphocytes. Markovic, S. N. & Murasko, D. M., *Cancer Research*, 51:1124 (1991). Stimulating murine NK lymphocyte activity by itself, however, is insufficient to eliminate established tumors. Markovic, S. N. & Murasko, D. M., *Int. J. Cancer*, 45:788 (1990). NK lymphocytes in anesthetized mice are transiently unresponsive to IFN-α and IFN-β. Markovic, S. N. and Murasko, D. M., *Clin. Immun.& Immunopath.*, 60:181–189 (1991), Markovic, S. N. & Murasko, D. M., *Clin. Immun.& Immunopath.*, 56:202–209 (1990), Markovic, S. N. and Murasko, D. M., *Cellular Immun.*, 151:474–480 (1993).

Combining surgical debulking of a primary tumor with neo-adjuvant administration of a mixture of IFN-α and IFN-β (IFN-α/β) in mice implanted with B16F10L tumor cells was successful in inducing complete remission/cure in more than 60% of the test mice that otherwise would have died of lung metastases. Markovic, S. N. & Murasko, D. M., *Int. Journal of Cancer*, 45:788 (1990). The observed antitumor effect of necadjuvant IFN-α/β therapy was mediated in mice by NK lymphocytes, which remained stimulated following surgery. Markovic, S. N. & Murasko, D. M., *Cancer Research*, 51:1124 (1991). Administering IFN-α/β postoperatively, on the other hand, was ineffective.

By identifying an IFN-α immunostimulatory dosage in humans, a combined therapy utilizing preoperative IFN-α therapy and surgical tumor resection can be used for treating resectable malignant tumors. As used herein, immunostimulatory dosages (ISD) are IFN-α dosages that increase NK lymphocyte cytotoxicity levels in a human.

Resectable malignant tumors include any solid tumor. Solid tumors, as used herein, refers to any malignant tumor that grows as a mass. Preferably, the resectable malignant tumor is an early-stage solid tumor. Early-stage solid tumors are solid tumors for which surgical resection results in complete removal of detectable tumor tissue in a patient as measured by current imaging techniques, e.g., CT scans or chest x-rays. Illustrative examples of resectable solid tumors include breast cancer, lung cancer, pancreatic cancer, brain tumors, prostate cancer, ovarian cancer, uterine cancer, renal cancer, melanoma and other solid tumor malignancies.

Although each tumor type may be amenable to surgical resection at different stages of growth, these stages are known.

Under certain circumstances, a localized malignant tumor may not be amenable to surgical resection. For example, the tumor may be in a location in the body that is not amenable to surgery or may not be at an appropriate growth stage. A solid tumor that is not amenable to surgical resection may be treated using a combined therapy utilizing immunostimulatory dosages of IFN-α and alternative tumor therapies. For example, immunostimulatory dosages of IFN-α can be combined with radiation therapy. The radiation therapy may reduce, diminish, or eliminate the solid tumor mass. Preferably, the solid tumor is an early-stage solid tumor.

A human can be administered an IFN-α composition prior to surgical resection or debulking of the tumor mass. The preoperative timing of administration and the ISD dosages of IFN-α can be designed to be effective for stimulating a patient's immune system and maintaining this stimulation following surgery. Such a therapy may provide a short, effective, low-toxicity, safe, out-patient based, and cost-effective method for treating resectable malignant tumors.

Surgical techniques to resect or debulk tumors are known, and include any accepted surgical technique useful for tumor removal.

The IFN-α composition may be one or more individual IFN-αs derived from any source and may include natural and/or recombinant IFN-α. The IFN-α composition can include, for example, a single isolated IFN-α or one or more IFN-αs that are combined to form a mixture of IFN-αs. Natural IFN-α compositions are IFN-αs that are isolated from animals, tissues or cells that naturally produce IFN-α. Recombinant IFN-α compositions are IFN-αs produced using recombinant DNA technologies.

An illustrative example of a natural IFN-α composition in accordance with the invention is the natural IFN-α composition sold under the trade designation ALFERON-N™, which is a mixture of IFN-αs ranging in molecular weight from 16 KD to 27 KD (approximately 166 amino acids). ALFERON-N™ is manufactured from pooled units of human peripheral blood leukocytes that have been induced with Sendai virus to produce IFN-α. ALFERON-N™ is available from Interferon Sciences, Inc., 783 Jersey Ave., New Brunswick, N.J. 08901. ALFERON-N™ is supplied as an injectable solution containing $5 \times 10^6$ U/ml IFN-α along with 3.3 mg/ml phenol and 1 mg/ml human albumin in a pH 7.4 maintained phosphate-buffered saline solution (8.0 mg/ml sodium chloride, 1.74 mg/ml sodium phosphate dibasic, 0.2 mg/ml potassium phosphate monobasic, and 0.2 mg/ml potassium chloride). ALFERON-N™ should be stored at 2–8° C. and must not be frozen or shaken.

Illustrative examples of recombinant IFN-αs include the IFN-αs sold under the trade designation INTRON-A™ available from Schering-Plough Corporation and ROFERON-A™ available from Hoffman-La Roche Corporation.

Useful IFN-α dosage levels include dosages that are immunostimulatory. To determine if an IFN-α dosage is an ISD, NK lymphocyte cytotoxicity levels can be measured according to the method of Whiteside et al., *J. Clin. Lab. Anal.*, 4:102–114 (1990). Increases in the NK lymphocyte cytotoxicity levels determined according to the Whiteside method can be identified at effector cell to target cell ratios (E:T) from about 3:1 to about 100:1. Typically, NK lymphocyte cytotoxicity level increases are identified at E:T ratios from about 15:1 to about 50:1. Other useful E:T ratios include 3:1, 6:1, 10:1, 12:1, 15:1, 25:1, 50:1, and 100:1. Preferably, the ISD increases NK lymphocyte cytotoxicity level at least about 50% compared to pretreatment NK lymphocyte cytotoxicity levels, i.e., baseline NK lymphocyte cytotoxicity level. In another preferred embodiment, the ISD increases NK lymphocyte cytotoxicity at least about 75% compared to pretreatment NK lymphocyte cytotoxicity levels.

Useful IFN-α dosages range from about 500 U/m$^2$ or less to about 4,000,000 U/m$^2$. Preferred IFN-α dosages include IFN-α dosages of about 3,000,000 U/m$^2$ or less, about 1,000,000 U/m$^2$ or less, about 500,000 U/m$^2$ or less, about 250,000 U/m$^2$ or less, and about 100,000 U/m$^2$ or less. Typically, IFN-α compositions are administered via intramuscular or subcutaneous injection. However, any accepted IFN-α delivery method is within the scope of the present invention.

Useful preoperative dosage schedules include administering IFN-α for at least five days before surgical resection of a malignancy. Preferably, the dosage schedule includes administering IFN-α for five consecutive days immediately preceding surgery, with surgery being on the sixth day. More preferably, the dosage schedule includes administering a single daily dosage of IFN-α for five consecutive days immediately prior to surgery, with surgery being on the sixth day. It is to be understood, however, that other dosage schedules resulting in the appropriate immunostimulation are also within the scope of the present invention.

A hematology analysis can be performed before and after administering IFN-α dosages. Diagnostic parameters measured before administering IFN-α can be considered baseline levels of a given parameter. The hematology analysis can include three types of diagnostic tests: immunophenotyping, blood counts and NK lymphocyte cytotoxicity. To perform the hematology analysis, 25 cc of blood can be drawn from a patient in an EDTA-treated VACUTAINER™ tube. The blood sample can be kept at room temperature until use, which is typically within two hours following collection. The blood sample can be divided into three samples: one for immunophenotyping, one for determining the blood counts and one for performing the NK lymphocyte cytotoxicity assay.

Immunophenotyping includes detecting changes in NK lymphocyte numbers, NK lymphocyte function, T-lymphocyte numbers, T-lymphocyte activation, B-lymphocyte numbers and B-lymphocyte activation. Changes in immune system parameters can be identified by using, for example, antibodies that recognize antigens specific to the above-identified lymphocytes according to the procedures found in the package inserts of the 1997 Beckton-Dickson Manual of Immunofluorescence. Lymphocyte phenotypic markers measured include absolute numbers for CD3, CD4, CD8, CD22 and CD16/56 and the state of activation for CD25, CD22, HLA-DR, CD65 and other specific activation markers.

Blood counts include complete blood counts (CBC) and differential blood count (Diff), which can be performed according to conventional clinical laboratory procedures and guidelines.

NK lymphocyte cytotoxicity can be assessed in vitro against Cr$^{51}$ labeled K562 target cells according to established protocols. Whiteside et al., *J. Clin. Lab. Anal.*, 4:102–114 (1990). Briefly, peripheral blood mononuclear cells obtained by venipuncture can be purified using gradient centrifugation. The mononuclear cells can be diluted to the three different concentrations and added to radiolabeled K562 cells in 96-well round bottom microtiter plates. Following a 4 hr incubation at 37° C. and 5% $CO_2$, the supernatants can be harvested and the radioactivity levels can be determined in a gamma counter (2 min counts/sample). Based on the obtained counts per minute (CPM), percent cytotoxicity and lytic unit (LI) calculations may be performed in accordance with conventional formulas. Changes in NK lymphocyte cytotoxicity may be determined by comparing NK lymphocyte cytotoxicity levels before and after administering IFN-α.

Typically, patients also undergo conventional clinical diagnostic evaluations including the following chemical parameters: absolute neutrophil count (ANC), alkaline phosphatase, aspartate transferase (AST), creatinine, direct bilirubin and total bilirubin. These diagnostics are affected by IFN-α and can reflect the toxicity of IFN-α therapy. Illustrative examples of the toxicities detected by these tests include liver toxicity, kidney toxicity and bone marrow toxicity.

At times, IFN-α may produce adverse side effects in patients. These side-effects typically involve flu-like symptoms. Examples of these symptoms can be found in the ALFERON-N™ injection package insert and accompanying material, which is available from Interferon Sciences, Inc. To monitor adverse side-effects, patients can undergo a toxicity evaluation. The toxicity evaluation can measure side-effect symptoms and detect any dose limiting toxicities (DLT) experienced by a volunteer. Side-effect symptoms can be evaluated according to NCI/CTC grading scales. The symptoms to be evaluated include fatigue, myalgias, anorexia, diarrhea, leukopenia, thrombocytopenia, vomiting, fevers, chills and abdominal pain. DLTs include a hematologic DLT, renal DLT or nonhematologic DLT. A hematologic DLT is defined as a grade 3 toxicity for $\geq 5$ days. A renal DLT is defined as serum creatine levels $\geq 2$ times baseline. Nonhematologic DLT is a toxicity $\geq$grade 3 as per Mayo/NCI Common Toxicity Criteria.

Administering an immunostimulatory dosage, as described herein, to a patient prior to undergoing surgery can stimulate the patient's immune system prior to surgery. Stimulating the patient's immune system prior to the patient receiving a pre-surgical anesthetic can prevent post-operative suppression of the patient's immune system. Preventing post-operative suppression of the patient's immune system can reduce the risk of postoperative infection.

An article of manufacture can include packaging material and an α-interferon composition contained within the packaging material. The α-interferon composition is effective for treating a human patient having a malignant tumor when an immunostimulatory dosage of the α-interferon composition is administered to the patient prior to surgical resection of the malignant tumor, then surgically resecting the malignant tumor. Also included with the packaging material is a label or package insert that indicates that administration of an immunostimulatory dosage of the α-interferon composition followed by surgical resection a malignant tumor is effective for treating a human patient having a malignant tumor. Any known packaging and printing method may be used to prepare the article of manufacture.

An article of manufacture can include packaging material and an α-interferon composition contained within the packaging material. The α-interferon composition is effective for treating a human patient having a malignant tumor when an immunostimulatory dosage of the α-interferon composition is administered to the patient in conjunction with effective non-surgical medical methods for diminishing malignant tumors. Also included with the packaging material is a label or package insert that indicates that administration of an immunostimulatory dosage of the α-interferon composition in conjunction with effective non-surgical medical methods for diminishing malignant tumors is effective for treating a human patient having a malignant tumor. Any known packaging and printing method may be used to prepare the article of manufacture.

The invention will be further understood with reference to the following illustrative embodiments, which are purely exemplary, and should not be taken as limiting the true scope of the present invention as described in the claims.

EXAMPLE 1

Identifying an Immunostimulatory Dosage for IFN-α

A peripheral blood sample (7–10 cc) was obtained from a healthy volunteer in an EDTA VACUTAINER™ tube. The volunteer was then given a single subcutaneous 250,000 U/m$^2$ dosage of ALFERON-N™ (lot #01-97-06) obtained from Interferon Sciences, Inc. The next day (18–24 hours post ALFERON-N™ dosage) a 7–10 cc peripheral blood sample was withdrawn using an EDTA VACUTAINER™ tube.

NK lymphocyte cytotoxicity levels were assessed in vitro for both blood samples. NK cell cytotoxicity was determined using $CR^{51}$ labeled K562 target cells according to the methods of Whiteside et al., *J. Clin. Lab. Anal.* 4:102 (1990). Briefly, peripheral blood mononuclear cells were isolated by gradient centrifugation (Ficol Hypaque, 1077, Sigma Chem. Co., St. Louis, Mo.). The mononuclear cells were diluted and added to $Cr^{51}$ radiolabeled K562 cells in 96 well round bottom microtiter plates. The cell mixture was incubated for four (4) hours at 37° C. and 5% $CO_2$. Supernatants resulting from the incubation were harvested using a SKATRON™ supernatant harvester. The radioactivity levels of the supernatants were quantitated for 2 minutes per sample in a gamma counter. The counts per minute (cpm) percent cytotoxicity for each supernatant sample was computed.

Figure 2:
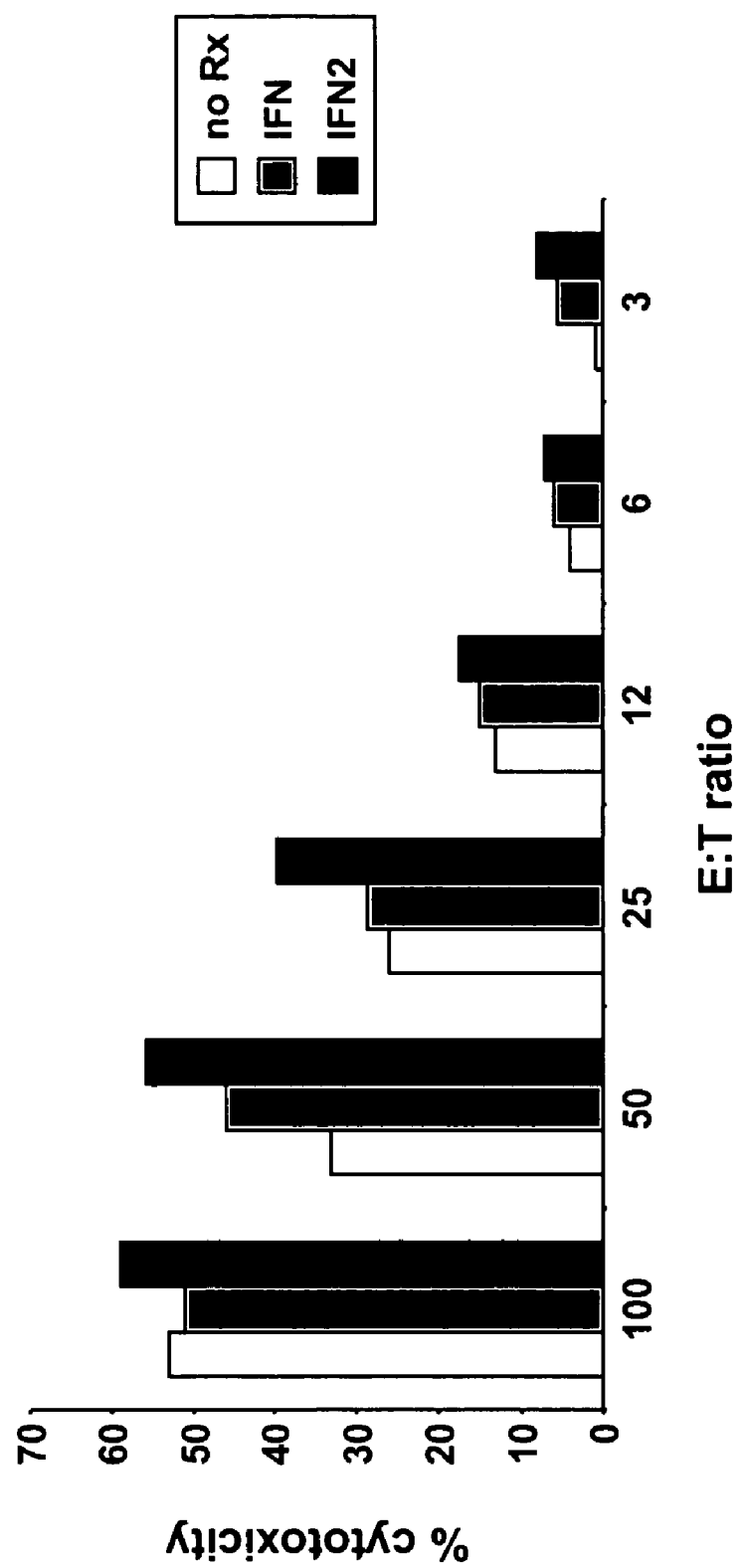
FIG. 2 is a graph depicting the increase in NK lymphocyte cytotoxicity levels at a variety of effector:target cell ratios after administering a low dosage of ALFERON-N™ to a human volunteer in vivo.
Figure 3:
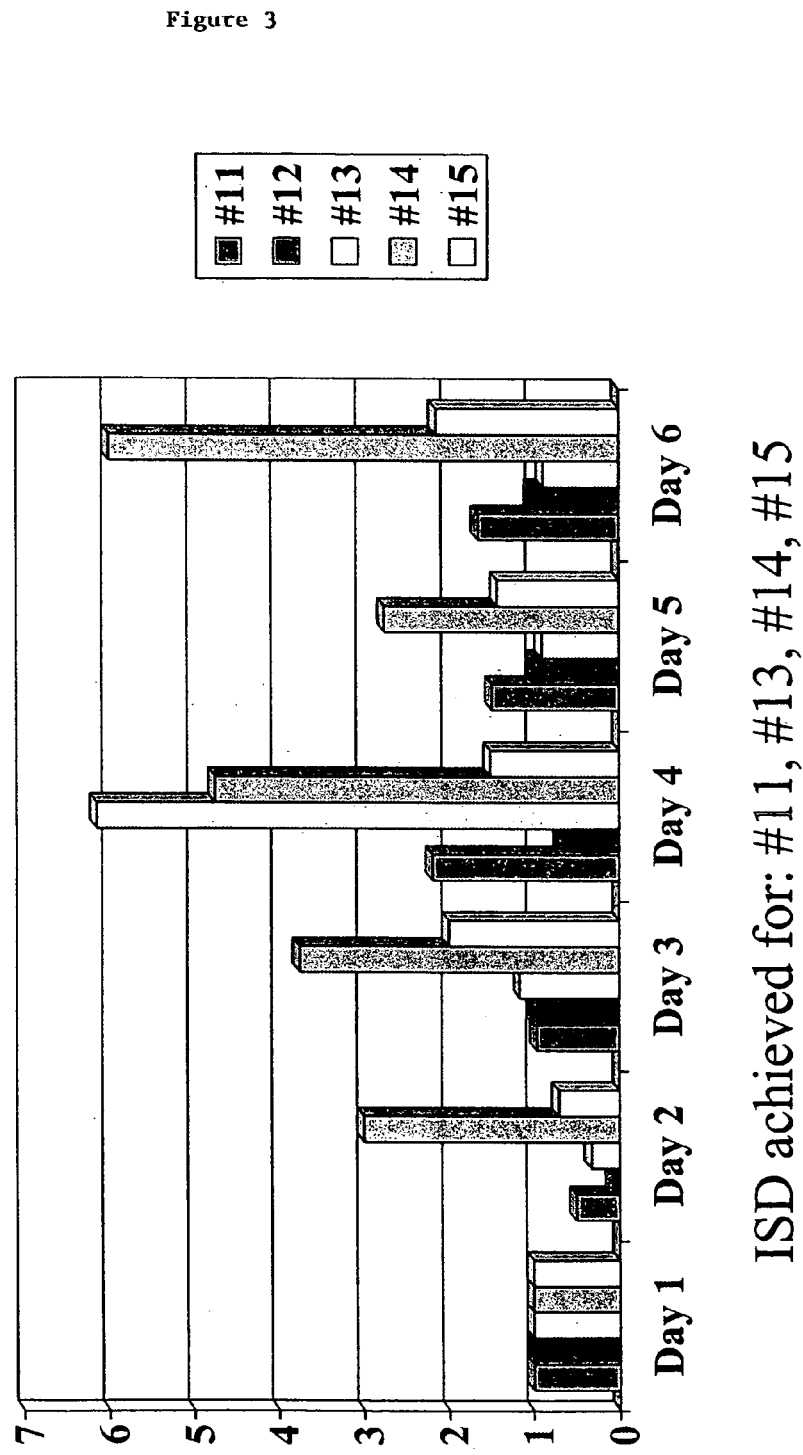

NK lymphocyte cytotoxicity was assessed at effector:target ratios (E:T ratio), i.e., mononuclear cell:K562 cell ratio, of 3:1, 6:1, 12:1, 25:1, 50:1, and 100:1. At a 3:1 effector:target ratio the baseline (pre-ALFERON-N™ dosage) NK lymphocyte cytotoxicity level was 0.8%. At a 25:1 effector:target ratio, the basal NK lymphocyte cytotoxicity level was 26%. At a 3:1 effector:target ratio, the NK lymphocyte cytotoxicity level was 5.5% for the NK lymphocytes harvested one day after the 250,000 U/m$^2$ ALFERON-N™ dosage. At a 25:1 effector:target ratio, the post-ALFERON-N™ dosage NK lymphocyte cytotoxicity level was 28.6%. The NK lymphocyte cytotoxicity level increase at the 25:1 ratio was 10% (((28.6%/26%)–1)*100). Graphical representations of the baseline and IFN-α stimulated NK lymphocyte cytotoxicity levels at E:T ratio of 3:1 and 25:1 are shown in FIG. 1. Graphical results for other E:T ratios measure NK lymphocyte cytotoxicity levels are shown in FIG. 2.

EXAMPLE 2

Identifying an Immunostimulatory Dosage for IFN-α

The volunteer of Example 1 was given a single subcutaneous 500,000 U/m$^2$ dosage of ALFERON-N™ (lot #01-97-06) seven days after receiving the ALFERON-N™ dosage of Example 1. Seven days was sufficient time to allow for the volunteer's baseline NK lymphocyte cytotoxicity level to return to the baseline levels of Example 1. The next day (18–24 hours post ALFERON-N™ dosage) a 7–10 cc peripheral blood sample was withdrawn using an EDTA VACUTAINER™ tube.

NK cell function was assessed in vitro for the blood sample. NK cell cytotoxicity was determined using $CR^{51}$ labeled K562 target cells according to the methods of Whiteside et al., *J. Clin. Lab. Anal.* 4:102 (1990), as described in Example 1.

At a 3:1 effector:target ratio, the post 500,000 U/m² ALFERON-N™ dosage NK lymphocyte cytotoxicity level was 8%. At a 25:1 effector:target ratio, the post 500,000 U/m² ALFERON-N™ dosage NK lymphocyte cytotoxicity level was 39.8%. The NK lymphocyte cytotoxicity level increase at the 25:1 ratio was 53% (((39.8%/26%)−1)*100). The NK lymphocyte cytotoxicity levels for the results of Example 2 are also indicated in FIG. 1 and FIG. 2.

EXAMPLE 3

Identifying an Immunostimulatory Dosage for IFN-α

Six to sixty volunteers are entered into two independent phase I trials to identify an immunostimulatory dosage (ISD) and observe any toxicities for ALFERON-N™. For purposes of the study, an ISD for ALFERON-N™ is the ALFERON-N™ dosage that increases NK lymphocyte cytotoxicity levels at least about 50% above the NK lymphocyte cytotoxicity levels measured prior to administration of ALFERON-N™ in at least two out of three volunteers evaluated at a given ALFERON-N™ dosage level.

Volunteers can consist of two groups: 1) healthy individuals and 2) volunteers who have a history of resected malignant melanoma. Melanoma volunteers should have been disease free for at least four months but less than five years.

Eligible volunteers should be at least 18 years of age, have a life expectancy greater than 12 weeks and be willing to return for a follow-up examination. Eligible volunteers can be selected to fall within the following clinical diagnostic parameters: ANC≧1500 µL, platelet counts≧100,000/µL, alkaline phosphatase≦3×UNL, AST≦3×UNL, Creatinine≦1.5×UNL and Total Bilirubin.

Eligible volunteers also should not have or have had a Eastern Co-operative Oncology Group performance status (ECOG) status 3 or 4, and should not have had an uncontrolled infection, chemotherapy ≦4 weeks, mitomycin C/nitrosoureas ≦6 weeks, immunotherapy ≦4 weeks, biologic therapy ≦4 weeks, radiation therapy ≦4 weeks, radiation to >25% of bone marrow, or treatment with antibiotics or antihistamines ≦4 weeks. In addition, failure to fully recover from the effects of prior chemotherapy regardless of interval since last treatment disqualifies a volunteer. The following conditions can also disqualify a volunteer: New York Heart Association classification of III or IV, CNS metastases, a seizure disorder, pregnancy, presently lactating, other concurrent chemotherapy, other concurrent immunotherapy, other concurrent radiotherapy, current evidence of malignancy, known chronic medical/psychiatric illnesses (such as diabetes, cirrhosis, chronic psychiatric conditions), known recent acute illnesses (including infections, allergic reactions, and autoimmune conditions) within the last 4 weeks, current/chronic use of medications, or known hypersensitivity to egg protein or neomycin.

Five eligible volunteers are entered at each dosage level, which is assigned according to Table 1. The first level evaluated is the 10,000 U/m² dosage (level 4). A dose escalation model is used to identify the ISD for ALFERON-N™ by proceeding step-wise up the dosage scale. That is, after the first five volunteers are evaluated, the next five volunteers enter at the next higher dosage level and so on.

TABLE 1

| ALFERON-N (TM) Dosages | |
|---|---|
| Dosage Level | ALFERON-N (TM) U/m² |
| 1 | 500 |
| 2 | 1000 |
| 3 | 5000 |
| 4 | 10,000 |
| 5 | 50,000 |
| 6 | 100,000 |
| 7 | 250,000 |
| 8 | 500,000 |
| 9 | 1,000,000 |
| 10 | 2,000,000 |
| 11 | 4,000,000 |

Each eligible volunteer entering the study undergoes a complete medical history, a standard physical examination including height, weight and performance status (PS), blood count, and clinical diagnostic chemistry evaluation within fourteen days preceding the volunteer's first ALFERON-N™ treatment. In addition to above-identified treatment, women volunteers of child bearing potential also undergo a serum pregnancy test within seven days prior to beginning the treatment schedule.

On day 1, each volunteer undergoes a hematology analysis, and then receives the volunteer's assigned intramuscular dosage of ALFERON-N™. On days 2 and 3 (24 and 48 hours post ALFERON-N™ treatment), each volunteer undergoes a hematology analysis, physical examination and a toxicity evaluation. Increases in NK lymphocyte cytotoxicity levels can be determined by comparing NK lymphocyte cytotoxicity levels measured on day 1 with the NK lymphocyte cytotoxicity levels measured on days 2 or 3. Two weeks after receiving ALFERON-N™, each volunteer receives another medical exam, blood count, creatinine clinical evaluation, and toxicity evaluation.

If a volunteer fails to complete the initial course of therapy, i.e., ALFERON-N™ administration and follow-up testing with 2 week observation, for any reason, the volunteer is regarded as treatment intolerant and an additional volunteer is treated at that dosage level.

Unless significant toxicities are observed, dose escalation continues until all dosage levels are exhausted. Significant toxicities are observed when 3 out of the 5 volunteers at a given dosage level experience a DLT. This dose escalation model creates an ALFERON-N™ dosage versus NK lymphocyte cytotoxicity level response curve, which facilitates identifying the optimal ALFERON-N™ dosage.

EXAMPLE 4

Identifying an Optimal Individualized IFN-α ISD

A patient who has a documented early-stage solid tumor has their baseline NK lymphocyte cytotoxicity level assessed as described above. Next, a single immunostimulatory dosage of ALFERON-N™ identified in Example 3 is administered to the patient. The patient's NK lymphocyte cytotoxicity level is again assessed twenty four hours following ALFERON-N™ administration.

If the patient's NK lymphocyte toxicity levels are at least about 50% higher than the patient's baseline NK lymphocyte cytotoxicity levels at an E:T ratio of 25:1, then the identified dosage is considered the individual's optimized ALFERON-N™ dosage. If the ALFERON-N™ dosage resulted in less than a 50% increase in NK lymphocyte cytotoxicity level, the patient is administered a second ALFERON-N™ dosage that is 2 standard deviations less than the mean ISD ALFERON-N™ dosage identified in Example 3. The second ALFERON-N™ dosage is administered after a five day wash-out period. If the second dosage is unsuccessful, the patient is administered a third ALFERON-N™ dosage that is 2 standard deviations more than the mean ISD ALFERON-N™ dosage. The third ALFERON-N™ dosage is also administered after a five day wash-out period. If the third ALFERON-N™ dosage does not result in at least about a 50% increase in NK lymphocyte cytotoxicity level, the ALFERON-N™ dosing is repeated at 1 standard deviation below and above the mean ISD ALFERON-N™ dosage identified in Example 3. Again, each dosing test is performed after a 5 day wash-out period. If the final treatment schedule does not result in at least about a 50% increase in NK lymphocyte cytotoxicity level, the patient is considered not to have an optimal ALFERON-N™ dosage.

EXAMPLE 5

Treating Patients with Immunostimulatory Dosages of IFN-α

Having identified an optimal ALFERON-N™ ISD, a patient suffering from a early-stage resectable malignancy is administered five injections of the optimal ALFERON-N™ dosage once per day for five days immediately prior to surgery. On the sixth day, the resectable malignancy is surgically resected according to accepted medical techniques. Post-operative hematology analysis is performed as described herein on days 1 and 7 following surgery. Thereafter, continued monitoring of the patient's progress is performed at regularly scheduled checkups every three months following surgery. In addition, post-operative monitoring and continued monitoring provides information concerning the incidence of post-operative infections in the patients, which can be reduced in patients receiving the immunostimulatory dosages of IFN-α as disclosed herein.

Other aspects, advantages, and modifications are within the scope of the following claims.

What is claimed is:

1. A method for stimulating the immune system of a human patient having a resectable malignant tumor, said method comprising:
   a) determining the natural killer lymphocyte cytotoxicity of said patient to provide a baseline natural killer lymphocyte cytotoxicity;
   b) administering an immunostimulatory dosage of an α-interferon composition to said patient, wherein said immunostimulatory dosage increases natural killer lymphocyte cytotoxicity at least about 75% above said baseline natural killer lymphocyte cytotoxicity; and
   c) surgically resecting said malignant tumor, wherein said immunostimulatory dosage is administered to said patient for about five days prior to resecting said malignant tumor.

2. A method for stimulating the immune system of a human patient having a resectable malignant tumor, said method comprising:
   a) determining the natural killer lymphocyte cytotoxicity of said patient to provide a baseline natural killer lymphocyte cytotoxicity;
   b) administering an immunostimulatory dosage of an α-interferon composition to said patient, wherein said immunostimulatory dosage increases natural killer lymphocyte cytotoxicity at least about 75% above said baseline natural killer lymphocyte cytotoxicity; and
   c) surgically resecting said malignant tumor, wherein said malignant tumor is an early-stage solid tumor wherein steps a), b) and c) are performed in sequential order.

3. A method for stimulating the immune system of a human patient having a resectable malignant tumor, said method comprising:
   a) determining the natural killer lymphocyte cytotoxicity of said patient to provide a baseline natural killer lymphocyte cytotoxicity;
   b) administering an immunostimulatory dosage of an α-interferon composition to said patient, wherein said immunostimulatory dosage increases natural killer lymphocyte cytotoxicity at least about 75% above said baseline natural killer lymphocyte cytotoxicity; and
   c) surgically resecting said malignant tumor, wherein said malignant tumor is a melanoma wherein steps a), b) and c) are performed in sequential order.

* * * * *